(12) United States Patent
Mule et al.

(10) Patent No.: US 8,597,946 B2
(45) Date of Patent: Dec. 3, 2013

(54) ENHANCED DENDRITIC CELLS FOR CANCER IMMUNOTHERAPY

(75) Inventors: James J. Mule, Odessa, FL (US); Shari A. Pilon-Thomas, Tampa, FL (US); Norimasa Matsushita, Hachiouji (JP); Annabelle Grolleau-Julius, Ann Arbor, MI (US)

(73) Assignees: H. Lee Moffitt Caner Center and Research Institute, Inc., Tampa, FL (US); The Regents of the University of Michigan, Ann Arbor, MI (US)

( * ) Notice: Subject to any disclaimer, the term of this patent is extended or adjusted under 35 U.S.C. 154(b) by 325 days.

(21) Appl. No.: 12/921,708

(22) PCT Filed: Mar. 10, 2009

(86) PCT No.: PCT/US2009/036689
§ 371 (c)(1),
(2), (4) Date: Nov. 23, 2010

(87) PCT Pub. No.: WO2009/114547
PCT Pub. Date: Sep. 17, 2009

(65) Prior Publication Data
US 2011/0059054 A1    Mar. 10, 2011

Related U.S. Application Data

(60) Provisional application No. 61/035,249, filed on Mar. 10, 2008, provisional application No. 61/118,119, filed on Nov. 26, 2008.

(51) Int. Cl.
*C12N 5/071* (2010.01)
*C12N 5/00* (2006.01)
*C12N 5/02* (2006.01)

(52) U.S. Cl.
USPC .......................................... 435/372; 435/377

(58) Field of Classification Search
None
See application file for complete search history.

(56) References Cited

PUBLICATIONS

Gavilondo, 2000, Biotechniques, vol. 29: 128-145.*
International Search Report and Written Opinion; Application No. PCT/US09/36689; mailed May 28, 2009; 10 pages.
Grolleau et al., "Inducible Expression of Macrophage Receptor Marco by Dendritic Cells Following Phagocytic Uptake of Dead Cells Uncovered by Oligonucleotide Arrays," J Immunol, 171:2879-2888, 2003.
Ernstoff et al., "Developing a Rational Tumor Vaccine Therapy for Renal Cell Carcinoma: Immune Yin and Yang," Clin Cancer Res, 13(2 Suppl) Jan. 15, 2007.
Prasad et al., "Dendritic Cells Loaded with Stressed Tumor Cells Elicit Long-Lasting protective Tumor Immunity in Mice Depleted of $CD4^+$ $CD25^+$ Regulatory T Cells," The Journal of Immunology, pp. 90-98, 2005.
Sankala et al., "Characterization of Recombinant Soluble Macrophage Scavenger Receptor Marco," The Journal of Biological Chemistry, vol. 277, No. 36, Sep. 6, 2002, pp. 33378-33385.

* cited by examiner

*Primary Examiner* — Amy Juedes
(74) *Attorney, Agent, or Firm* — Fish & Richardson P.C.

(57) ABSTRACT

Described herein are methods of cancer immunotherapy, particularly methods of preparing a population of enhanced dendritic cells and methods of treating cancer using the enhanced dendritic cells.

13 Claims, 8 Drawing Sheets

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Primer

```
<400> SEQUENCE: 1
gcactgctgc tgattcaagt tc                                              22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agttgctcct ggctggtatg                                                 20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
aaatcaatgt tccaaagccc aagaa                                           25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cctgttgctc catctcgtcc catag                                           25
```

ENHANCED DENDRITIC CELLS FOR CANCER IMMUNOTHERAPY

CROSS REFERENCE TO RELATED APPLICATIONS

This application is a National Stage Application of International Patent Application No. PCT/US2009/036689, filed on Mar. 10, 2009, which claims the benefit of U.S. Provisional Application Ser. No. 61/035,249, filed on Mar. 10, 2008, and U.S. Provisional Application Ser. No. 61/118,119, filed on Nov. 26, 2008. The entire contents of the foregoing are incorporated herein by reference.

STATEMENT REGARDING FEDERALLY SPONSORED RESEARCH OR DEVELOPMENT

This invention was made with government support under Grant No. CA071669 awarded by the National Institutes of Health. The government has certain rights in the invention.

TECHNICAL FIELD

The technology described herein generally relates to methods of cancer immunotherapy. The technology more particularly relates to methods of preparing a population of enhanced dendritic cells and methods of treating cancer using the enhanced dendritic cells.

BACKGROUND

A number of strategies involving the use of dendritic cells (DC) for inducing specific anti-tumor immune responses are being investigated. The use of DC "loaded" with dead cancer cells in vaccine (immunotherapy) approaches has been described in both experimental and clinical settings (see, e.g., Fields et al., Proc Natl Acad Sci USA 95:9482 (1998); Asavaroengchai et al., Proc Natl Acad Sci USA 99:931 (2002); Chang et al., Clin Cancer Res 8:1021 (2002); Geiger et al., Cancer Res 61:8513 (2001)) and others (Eggert et al., Cancer Res 59:3340 (1999); Morse et al., Cancer Res 59:56 (1999); Steinman et al., Nature 449:419 (2007); Steinman, Nature Med 13:1155 (2007)). DC pulsed with tumor-associated antigen(s) in the form of dead tumor cells (denoted TP-DC) can elicit specific T cell proliferation and CTL reactivity, and have shown efficacy in protecting naive mice from tumor challenge and in reducing the growth of tumors in vivo.

SUMMARY

At least in part, the present invention is based on the discovery that treating dead tumor cell-pulsed dendritic cells (TP-DC) with an anti-MARCO antibody improves the efficacy of cancer immunotherapy using dendritic cells. As one theory, not meant to be limiting, this increase in efficacy may be due to an increased percentage of the antibody-treated TP-DC (referred to herein as "enhanced DC") being trafficked to the lymph nodes.

In general, the invention features methods for preparing a population of enhanced dendritic cells. The methods include obtaining an initial enriched population of dendritic cells, and contacting the dendritic cells with dead tumor cells and an antibody or antigen-binding fragment that binds to macrophage receptor with collagenous structure (MARCO). In some embodiments, the initial enriched population of dendritic cells is from bone marrow, umbilical cord blood, or peripheral blood. In some embodiments, the dead tumor cells are from a solid or hematopoietic-derived tumor, for example, neuroblastoma, sarcoma, melanoma, and renal cell tumors. In some embodiments, the dead tumor cells are from a tumor in the subject, or from a cancer of the same type as the cancer in the subject, for example, from another subject having the same type of cancer, or from a cell line made from cells of a cancer of the same type as the cancer in the subject. In some embodiments, the antibody or antigen-binding fragment thereof binds to the carboxyl-terminal cysteine-rich domain V of MARCO. In some embodiments, the anti-MARCO antibody is a humanized or human antibody.

The invention also features the use of a population of enhanced dendritic cells described herein as a medicament for the treatment of a cancer, or in the manufacture of a medicament for the treatment of cancer.

In another aspect, the invention features methods for treating a cancer in a subject, e.g., enhancing or inducing immune response to a cancer and clinical efficacy. The methods include obtaining an initial enriched population of dendritic cells from the subject, contacting the initial enriched population of dendritic cells with dead tumor cells and an antibody or antigen-binding fragment that binds to MARCO, and administering to the subject a therapeutically effective amount of the enhanced dendritic cells, to thereby treat the cancer in the subject. In some embodiments, the cancer is a solid or hematopoietic-derived tumor type, for example, neuroblastoma, melanoma, sarcoma, and renal cell cancers. In some embodiments, the dead tumor cells are from a tumor in the subject, or from a cancer of the same type as the cancer in the subject, for example, from another subject having the same type of cancer, or from a cell line made from cells of a cancer of the same type as the cancer in the subject.

In some embodiments, the subject is a non-human animal (e.g., a mammal) or a human. In some embodiments, the route of administration is subcutaneous, intradermal, or subdermal.

The subject can be treated with the enhanced dendritic cells as a monotherapy or in combination with one or more additional treatments. One or multiple doses of the enhanced dendritic cells can be administered. Furthermore, subjects having a cancer can be identified for this treatment and monitored for tumor growth, tumor regrowth, or survival during and after treatment.

Throughout the description and claims of the specification the word "comprise" and variations thereof, such as "comprising" and "comprises", is not intended to exclude other additives, components, integers or steps.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

In FIG. 8A, open and solid bars represent T cells alone and T cells plus B16 TP-DC, respectively. Representative of two experiments.

DETAILED DESCRIPTION

Figure 1:
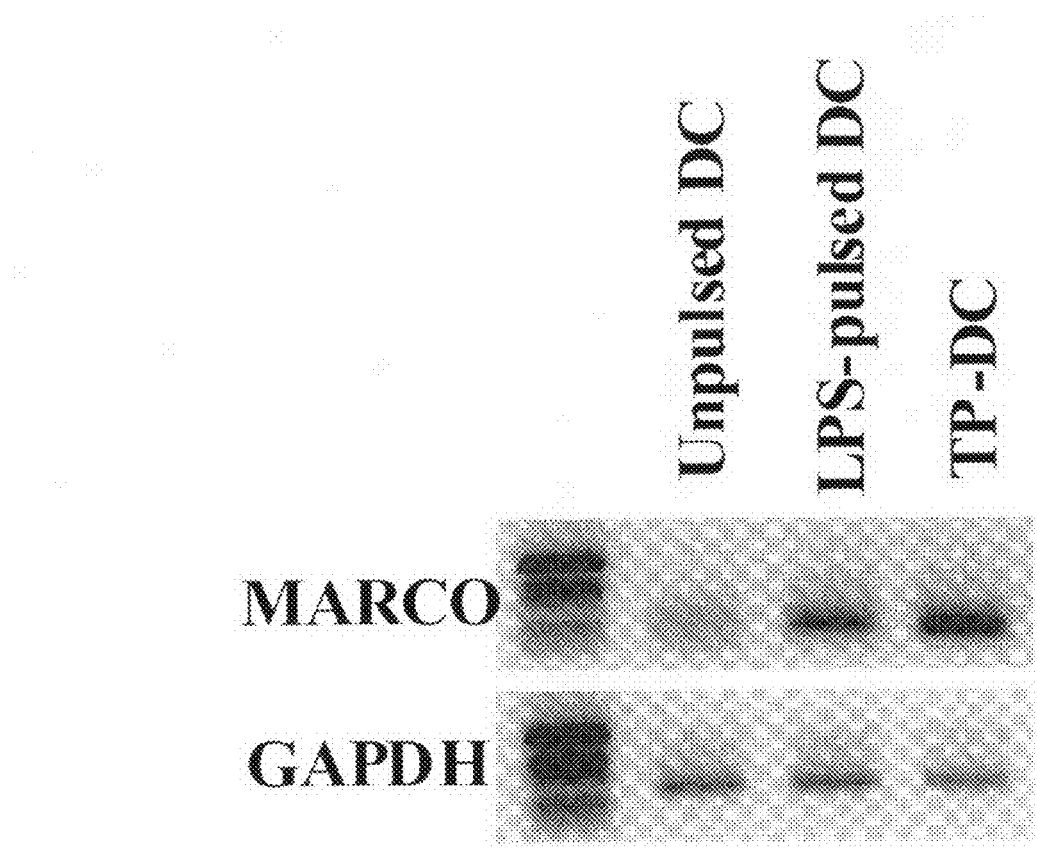
FIG. 1 is an image of a gel showing MARCO mRNA expression by DC loaded with LPS or loaded with tumor lysate. Total RNA from unpulsed (UP)-DC and DC pulsed with LPS or loaded with B16 melanoma lysate as indicated, were analyzed by RT-PCR for MARCO transcript expression. Amounts of mRNA were adjusted to give comparable GAPDH signals. The experiment was repeated twice with similar results.

The efficacy of cancer immunotherapy using dead tumor cell-pulsed dendritic cells (TP-DC) can be significantly increased by treating the TP-DC with an antibody to MARCO. These treated cells are referred to herein as "enhanced DC." Described herein are compositions including the enhanced DC, as well as methods for treating cancer, e.g., by eliciting an anti-tumor immune response in a subject.

Precedent exists for monoclonal antibodies altering the trafficking of immune cells in vivo based on the biology of the targeted surface molecule. For example, the widely used macrophage antibody 5C6 has been shown to profoundly influence inflammatory cell recruitment in vivo (Rosen et al., J Exp Med 166:1685 (1987)). Ex vivo generated DC in both mouse and humans have very limited movement from subcutaneous or intradermal injection sites to locally draining lymph node(s) and essentially none to spleen (Adema et al., Curr Opin Immunol 17:170 (2005); Verdijk et al., Expert Opin Biol Ther 8:865 (2008)). This limitation is considered to be one of the significant weaknesses in the use of DC-based vaccines to date. It is also clear that the intravenous route of administration of DC has proven ineffective to target multiple peripheral lymphoid organs as well. Most DC administered by this route appear to be trapped rapidly in the capillaries of the lungs, in the spleen, and in the liver where the DC then tend to be cleared. Immunization by this route is generally inadequate and some investigators have abandoned the intravenous delivery of DC both in animal studies and in human clinical trials. Recently, the direct intranodal delivery of antigen-loaded DC has gained much favor, as this route appears to be somewhat superior for inducing immune responses compared to the subcutaneous or intradermal route (Adema et al., Curr Opin Immunol 17:170 (2005); Verdijk et al., Expert Opin Biol Ther 8:865 (2008); Lambert et al., Cancer Res. 61:641 (2001)). However, it is logistically and technically impractical to deliver a large number of DC to a single lymph node as well as to target multiple lymph nodes by the current methodology.

Methods of Preparing Enhanced Dendritic Cells

In general, the enhanced dendritic cells described herein are prepared by treating dendritic cells with both dead tumor cells and an anti-MARCO antibody.

Dead Tumor Cells

As used herein, a composition comprising "dead tumor cells" is a suspension of either lysed tumor cells, fragments of tumor cells, or tumor cells that remain substantially intact following exposure to UV irradiation or gamma irradiation. Any method known in the art can be used for preparing dead tumor cells, so long as the dead tumor cells retain tumor-specific antigens, e.g., antigens expressed on the surface of the tumor cells. See, e.g., Chang et al., Clin Cancer Res 8:1021 (2002); Geiger et al., Cancer Res 61:8513 (2001). The tumor cells can be from solid or liquid tumors. The composition can be in any carrier suitable for injection, e.g., a buffered saline.

For example, tumors can be harvested surgically from subjects. The harvested tumors can be used freshly or cryopreserved for later use. A single cell suspension can be made by a combination of mechanical and enzyme dispersion techniques. Tumor cell lines can also be generated. For long-term storage, tumor cells can be frozen in a liquid nitrogen freezer.

Tumor cells can be lysed in suspension by repeated freeze-thaw cycles in rapid succession or killed and remain intact following UV or gamma irradiation. The lysed cells are irradiated and stored in liquid nitrogen for later use (see, e.g., Example 6, herein). The tumor cells will preferably be obtained from the subject to whom they will be delivered, i.e., autologous, or from another subject having the same type of cancer. In some embodiments, the methods include obtaining a sample of a tumor in a subject to be treated using a method described herein, and detecting the presence of tumor-associated antigens on cells of the tumor. Then, a cells from a tumor in another subject, or from a combination of tumors in other subjects, can be chosen that express the same tumor-associated antigens. A number of tumor-associated antigens are known in the art, and methods for detecting them are well known.

In some embodiments, the dead tumor cells are obtained from a cell line made from cells of a tumor that is from the same type of cancer that the subject has, e.g., a breast cancer cell line for use in a subject who has breast cancer. Cancer cell lines are known in the art, and numerous examples are commercially available, e.g., from the American Type Culture Collection (ATCC) (Manassas, Va.), which has over 1100 different tumor cell lines from a variety of species. In some embodiments, the methods include obtaining a sample of a tumor in a subject to be treated using a method described herein, and detecting the presence of tumor-associated antigens on cells of the tumor. Then, a tumor cell line or a combination of tumor cell lines can be chosen that express the same tumor-associated antigens. A number of tumor-associated antigens are known in the art, and methods for detecting them are well known.

MARCO

Global gene analysis uncovered distinct changes in gene expression patterns as a consequence of dead tumor cell loading of DC (Grolleau et al., J Immunol 171:2879 (2003)). Most of the affected genes encoded a repertoire of proteins important for DC effector functions including cytokines, chemokines and receptors, antigen presentation, cell adhesion, and T cell activation. The most highly expressed transcript in TP-DC was shown to encode for macrophage receptor with collagenous structure (MARCO), a class A scavenger receptor (SR-A) (Granucci et al., Blood 102:2940 (2003); Re et al., J Immunol 169: 2264 (2002)). However, the role of MARCO in the TP-DC, and what effect it might have on efficacy of tumor therapy, was unknown.

MARCO is an integral membrane component composed of three 52-kDa monomers (Elomaa et al., Cell 80:603 (1995); Elomaa et al., J Biol Chem 273:4530 (1998)). Similar to the other SR-As, MARCO has a binding activity against Gram-positive and negative bacteria (van der Laan et al., J Immunol 162:939 (1999); van der Laan et al., Immunol Lett 57:203 (1997); Arredouani et al., J Immunol 175:6058 (2005); Elshourbagy et al., Eur J Biochem 267:919 (2000); Kraal et al., Microbes Infect 2: 313 (2000); Mukhopadhyay et al., Eur J Immunol 36:940 (2006)), modified low density lipoproteins (Elomaa et al., Cell 80:603 (1995); Kraal et al., Microbes Infect 2: 313 (2000)), as well as oxide and other particles (Arredouani et al., J Immunol 175:6058 (2005); Palecanda et al., J Exp Med 189:1497 (1999); Arredouani et al., J Exp Med 200:267 (2004)). MARCO expression was earlier identified in a subpopulation of macrophages in the marginal zone of the spleen and in the lymph node of the medullary cord (Elomaa et al., Cell 80:603 (1995)), and its expression was found to be up-regulated by bacterial LPS (van der Laan et al., Immunol Lett 57:203 (1997)) or systemic bacterial sepsis (van der Laan et al., J Immunol 162:939 (1999); van der Laan et al., Immunol Lett 57:203 (1997); Yoshimatsu et al., Int J Exp Pathol 85:335 (2004)). Further, MARCO is thought to play an important role in macrophage participation in some immune responses by mediating binding and phagocytosis, but also in the formation of lamellipodia-like structures and of dendritic processes. It has been reported that scavenger receptors have avid adherence to matrix molecules and to other cells (el Khoury et al., J Biol Chem 269:10197 (1994); Gowen et al., Matrix Biol 19:61 (2000); Karlsson et al., J Exp Med 198:333 (2003)). In an allergic airway inflammation model, scavenger receptor deficient innate DC revealed a higher level of migration into thoracic lymph nodes than control, wild-type DC (Arredouani et al., J Immunol 178:5912 (2007)).

Exemplary nucleic acid sequences for MARCO are NM_006770.3 for human, NM_010766.2 for mouse, and NM_001109011.1 for rat. Exemplary amino acid sequences for MARCO are NP_006761.1 for human, NP_034896.1 for mouse, and NP_001102481.1 for rat.

Anti-MARCO Antibodies

Anti-MARCO antibodies suitable for use in the present methods are known in the art and/or are commercially available. For example, anti-MARCO antibodies are commercially available from Hycult biotechnology by; Abcam; AbD Serotec; Abnova Corporation; Thermo Scientific; Acris Antibodies GmbH; BACHEM; BMA Biomedicals; Cell Sciences; GenWay Biotech, Inc.; LifeSpan BioSciences; Novus Biologicals; R&D Systems; Raybiotech, Inc.; and Santa Cruz Biotechnology, Inc. The ED31 antibody used herein is available from Novus Biologicals and is described in, e.g., van der Laan et al. J. Immunol. 162: 939-947 (1999); and van der Laan et al., Immunol. Letters 57: 203-208 (1997). An anti-human MARCO antibody is described in Elomaa et al., J. Biol. Chem., 273(8):4530-4538 (1998). Alternatively, anti-MARCO antibodies can be made by the various methods known in the art.

In some embodiments, the anti-MARCO antibody or antigen-binding fragment thereof binds to the carboxyl-terminal cysteine-rich domain V of MARCO (residues 421-520 of the human MARCO polypeptide, see Elomaa et al., J. Biol. Chem., 273(8):4530-4538 (1998)). This domain is believed to be the ligand binding domain, and in some embodiments the anti-MARCO antibody blocks ligand binding to MARCO. Methods for determining whether an antibody binds to a particular region of a protein, and for determining whether antibody binding blocks ligand binding, are known in the art, e.g., peptide binding assays and competitive binding assays.

In some embodiments, the anti-MARCO antibody or antigen-binding fragment thereof increases or elicits MARCO signalling through p38, and decreases ERK signalling.

The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments, which retain the ability to bind antigen.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. The antibody can be monovalent or bivalent.

Methods for making suitable antibodies are known in the art. A full-length antigen or antigenic peptide fragment thereof can be used as an immunogen, or can be used to identify antibodies made with other immunogens, e.g., cells, membrane preparations, and the like, e.g., E rosette positive purified normal human peripheral T cells, as described in U.S. Pat. Nos. 4,361,549 and 4,654,210.

Methods for making monoclonal antibodies are known in the art. Basically, the process involves obtaining antibody-secreting immune cells (lymphocytes) from the spleen of a mammal (e.g., mouse) that has been previously immunized with the antigen of interest either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Mammalian lymphocytes can be immunized by in vivo immunization of an animal (e.g., a mouse) with an antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. See, e.g., Harlow, et. al., editors, *Antibodies: A Laboratory Manual* (1988).

In addition to utilizing whole (bivalent) antibodies, the invention encompasses the use of binding portions of such antibodies. Such binding portions include Fab fragments, F(ab')$_2$ fragments, and Fv fragments. Such fragments can be obtained commercially, or using methods known in the art, e.g., as described in *Monoclonal Antibodies: Methods and Protocols* (*Methods in Molecular Biology*), Albiter, ed., Humana Press; 1st edition (2007). For example, F(ab)$_2$ fragments can be generated by treating the antibody with an enzyme such as pepsin, a non-specific endopeptidase that normally produces one F(ab)$_2$ fragment and numerous small peptides of the Fc portion. The resulting F(ab)$_2$ fragment is composed of two disulfide-connected Fab units. The Fc fragment is extensively degraded and can be separated from the F(ab)$_2$ by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., BioExpress, West Lebanon, N.H.

Chimeric, humanized, de-immunized, or completely human antibodies are desirable for applications which include repeated administration.

Chimeric antibodies generally contain portions of two different antibodies, typically of two different species. Generally, such antibodies contain human constant regions and variable regions from another species, e.g., murine variable regions. For example, mouse/human chimeric antibodies have been reported which exhibit binding characteristics of the parental mouse antibody, and effector functions associated with the human constant region. See, e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al., Cancer Research, 47:999 (1987)). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line. Such chimeric antibodies have been used in human therapy.

Humanized antibodies are known in the art. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al., Proc. Natl. Acad. Sci., USA 81:6801 (1984); Morrison and Oi, Adv. Immunol. 44:65 (1988) (which preserves the ligand-binding properties, but which also retains the immunogenicity of the nonhuman variable domains); (b) by grafting only the non-human CDRs onto human framework and constant regions with or without retention of critical framework residues (Jones et al. Nature, 321:522 (1986); Verhoeyen et al., Science 239:1539 (1988)); or (c) by transplanting the entire nonhuman variable domains (to preserve ligand-binding properties) but also "cloaking" them with a human-like surface through judicious replacement of exposed residues (to reduce antigenicity) (Padlan, Molec. Immunol. 28:489 (1991)).

Humanization by CDR grafting typically involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al., Nature 332:323

(1988); Queen et al., Proc. Natl. Acad. Sci. USA 86:10,029 (1989)). The framework residues which need to be preserved can be identified by computer modeling. Alternatively, critical framework residues may potentially be identified by comparing known antibody combining site structures (Padlan, Molec. Immun. 31(3):169-217 (1994)). The invention also includes partially humanized antibodies, in which the 6 CDRs of the heavy and light chains and a limited number of structural amino acids of the murine monoclonal antibody are grafted by recombinant technology to the CDR-depleted human IgG scaffold (Jones et al., Nature 321:522-525 (1986)).

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody (Biovation, Aberdeen, Scotland).

The antibody can also be a single chain antibody. A single-chain antibody (scFV) can be engineered (see, for example, Colcher et al., Ann. N.Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31 (1994), incorporated herein by reference.

Dendritic Cells (DC)

Dendritic cells (DC) are highly potent antigen-presenting cells of bone marrow origin that are integral in the stimulation of primary and secondary T- and B-cell responses. DC can be prepared from peripheral blood, umbilical cord blood, or bone marrow using methods known in the art, e.g., as described in Bernhard et al., Cancer Res, 55:1099 (1995); Chang et al., Clin Cancer Res 8:1021 (2002); and Geiger et al., Cancer Res 61:8513 (2001) (see also Example 6 herein). In some embodiments, the DC are obtained from $CD34^+$ hematopoietic progenitor cells derived from bone marrow or granulocyte-colony stimulating factor-mobilized peripheral blood, e.g., as described in Bernhard et al., Cancer Res, 55:1099 (1995); thus the methods described herein can include a step of obtaining a sample comprising bone marrow or peripheral blood from a subject, and preparing an enriched population of DC therefrom using known methods. Optionally, an effective amount of a progenitor cell mobilizing agent, e.g., G-CSF, can be administered to the subject before the sample of blood is obtained, e.g., as described in Bernhard et al., Cancer Res, 55:1099 (1995). DC can also be derived and expanded from $CD34^+$ hematopoietic progenitor cells in umbilical cord blood by inducing dendritic cell differentiation and proliferation with GM-CSF plus TNF-alpha (see, e.g., Caux et al., Nature (Lond.) 360:258-261 (1992)). In some preferred embodiments, the DC are obtained from $CD14^+$ monocytes, e.g., as described in Chang et al., Clin Cancer Res 8:1021 (2002); and Geiger et al., Cancer Res 61:8513 (2001) (see also Example 6 herein).

The population of enriched derived DC will have at least about 50% (i.e., the population of cells includes at least about 50%) DC, or at least 60%, 70%, 80%, 90%, or more DC. Thus a population of cells that is at least about 50% DC is considered to be "enriched," as used herein As one of skill in the art would appreciate, the presence of other cells, e.g., other blood cells, in the preparation does not generally affect the therapeutic efficacy or usefulness of the DC. As used herein, "about" indicates a value plus or minus up to 5%.

In general, the methods described herein will use DC obtained from a patient to whom they will be administered, i.e., autologous DC. In some embodiments, DC from a very closely matched donor may be used, e.g., a donor who is so closely matched that no immune suppression, or only very minimal suppression, would be needed.

Treating Dendritic Cells to Prepare Enhanced Dendritic Cells

In some embodiments of the present methods, an enriched DC suspension is pulsed with dead tumor cells and treated with anti-MARCO antibody in culture medium either concurrently or consecutively (i.e., the DC can be contacted first with either the dead tumor cells or the antibody, or both can be used at the same time to produce enhanced DC). In general, the enhanced DC will be maintained under conditions sufficient to sustain the viability of the DC. Such conditions are known in the art. See, e.g., Chang et al., Clin Cancer Res 8:1021 (2002); and Geiger et al., Cancer Res 61:8513 (2001).

In general, the cell equivalent ratio of dead tumor cells (i.e., number of dead tumor cells for loading/pulsing of the DC) to DC will range from about 1:1 to 5:1, e.g., 1:1 or 3:1. In some embodiments, the concentration of anti-MARCO antibody will range from about 1 µg/mL to 100 µg/ml, e.g., 10 µg/ml, 20 µg/ml or 50 µg/ml. The cell suspension can be incubated at 37° C., 5% $CO_2$ for 12 to 48 hours, e.g., about 12-24 hours, in the presence of the dead tumor cells and anti-MARCO antibody to produce enhanced DC. After incubation, the dead tumor cell-pulsed and anti-MARCO antibody-treated DC (i.e. enhanced DC) are harvested and counted. The enhanced DC suspension can be adjusted to a total volume of 0.5 ml of PBS at about $2 \times 10^7$ cells/ml. For higher dose levels of enhanced DC, the cell suspension can be divided into several separate fractions each containing 0.5 ml for administration. (See Example 6, herein.)

Methods of Treating Cancer Using Enhanced Dendritic Cells

The methods described herein include methods for the treatment of cancer. Generally, the methods include administering a therapeutically effective amount of therapeutic agent as described herein, to a subject who is in need of, or who has been determined to be in need of, such treatment. As used herein, the term "treat" means to decrease the growth or growth rate of a tumor, prevent or delay re-growth of a tumor, e.g., a tumor that was debulked, e.g., surgically debulked, or treated using radiation or chemotherapy, or to decrease the size of a tumor. The methods of treatment include initiating or enhancing an anti-tumor immune response in the subject.

DC pulsed with a tumor antigen have been shown to elicit specific tumor-reactive T cells in preclinical and clinical studies, and to have clinical efficacy in patients. A number of Phase I and early Phase II clinical trials have shown that DC presenting tumor-associated antigens can lead to partial or complete regression of tumors (see, e.g., Hsu et al., Nat. Med., 2: 52-58 (1996) (B-cell lymphoma); Nestle et al., Nat. Med., 4: 328-332 (1998) (melanoma); Thurner et al., J. Exp. Med., 190: 1669-1678, (1999) (advanced stage 1V melanoma); Lim and Bailey-Wood, Int. J. Cancer, 83: 215-222 (1999) (multiple myeloma); Tjoa and Murphy, Semin. Surg. Oncol., 18: 80-87 (2000) (prostate cancer); Geiger et al., Lancet, 356: 1163-1165 (2000) (solid tumors in children); Chang et al., Clin Cancer Res 8:1021 (2002) (various stage IV solid malignancies); and Geiger et al., Cancer Res 61:8513 (2001) (pediatric solid tumor patients); Yu et al., Cancer Res. 64(14):4973-4979 (2004)(malignant glioma); Lopez et al., J Clin Oncol. 27(6):945-52 (2009), Epub 2009 Jan. 12 (melanoma); Lepisto et al., J Clin Oncol. 27(6):945-52 (2009, Epub 2009 Jan. 12 (pancreatic and biliary tumors); Yu et al., Viral Immunol. 21(4):435-42 (2008) (ovarian cancer); Burgdorf et al., Oncol Rep. 20(6):1305-11 (2008) (colorectal cancer);

Schuetz et al., Cancer Immunol Immunother. 2008 Nov. 8 (breast cancer); Palmer et al., Hepatology. 49(1):124-32 (2009) (hepatocellular carcinoma); Mackell et al., Clin Cancer Res. 14(15):4850-8 (2008) (pediatric Sarcoma/Ewing's sarcoma). See also Weber and Schulz, Princ. Pract. Biol. Ther. Cancer, 1: 2-11,2000; Palucka et al., J. Immunother. 31(9): 793-805 (2008); Palucka et al., Immunol Rev. 220:129-50 (2007). The methods described herein can be used to treat any of these cancers, as well as any cancer that presents an antigen recognizable by the immune system.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers treated by the methods described herein include those that are particularly immunogenic, e.g., neuroblastoma, melanoma, and renal cell cancer.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. For example, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The enhanced dendritic cells described herein can be administered to a subject, e.g., a cancer patient, by a variety of routes. For example, subcutaneous, intradermal, or subdermal.

Data obtained from in vitro cell cultures and animal models can be used to project an efficacious dose regimen in humans, including dose and frequency. A projected optimal human efficacious dose regimen can be selected and further tested in clinical trials.

In general, efficacious dose regimen (dose and frequency) ranges for the enhanced dendritic cells include amounts sufficient to treat cancers. Such doses include, e.g., about $1 \times 10^5$ dendritic cells to $1 \times 10^8$ dendritic cells per dose, e.g., about $0.5 \times 10^6$ enhanced dendritic cells to $1 \times 10^7$ enhanced dendritic cells per dose, e.g., about $1 \times 10^6$ enhanced dendritic cells per dose. These numbers are general guidelines, which one of skill in the art can use to determine optimal dosing. Suitable dose frequencies include, e.g., every 2 weeks for 3 doses, every week for 12 doses; or every other week for four doses. In some embodiments, a dose is administered every few days for a week (for 2-3 doses in a week), and then additional doses are administered once a month or every 2-3 weeks. The treatment can also be resumed after a certain period if needed. The dose regimen, including both dose and frequency, can be adjusted based on the genetic, demographic, and pathophysiological characteristics of the subject, and disease status. For example, the age, sex, and weight of a subject to be treated, and the type or severity of the subject's cancer. Other factors that can affect the dose regimen include the general health of the subject, other disorders concurrently or previously affecting the subject, and other concurrent treatments.

The dose of enhanced dendritic cells can be flat (e.g., in cells/dose) or individualized (e.g., in cells/kg or cells/m$^2$ dose) based on the safety and efficacy of the treatment and the condition of the subject. The dose and frequency can also be further individualized based on the tumor burden of the subject (e.g., in cells/tumor size, cells/kg/tumor size or cells/m$^2$/tumor size dose). It should also be understood that a specific dose regimen for any particular subject can depend upon the judgment of the treating medical practitioner. In determining the effective amount of the cells to be administered, the treating medical practitioner can evaluate factors such as adverse events, and/or the progression of the disease.

Combination Therapy

The enhanced dendritic cells described herein can be used as a monotherapy or as part of a multi-modal therapeutic regimen. The enhanced dendritic cells can be administered to a subject in combination with other treatment modalities with different mechanisms of action, for example, surgery, radiation, cytotoxic chemotherapy (e.g., cyclophosphamide, 5-fluorouracil, cisplatin, gemcitabine), targeted biologic agents (e.g., monoclonal antibodies, fusion proteins), and immune modulators (e.g., cytokines and/or CTLA-4, PDL-1, PD-1 antibodies). These combination therapies can have additive or synergistic effects. The enhanced dendritic cells can also be used in combination with other cancer vaccines that carry different tumor-associated antigens. The various treatments can be administered concurrently or sequentially (e.g., before or after treatment using a method described herein). For example, one treatment can be given first, followed by the initiation of administration of other treatments after some time. A previous therapy can be maintained until another treatment or treatments have effect or reach an efficacious level.

In one example, a surgical treatment method is administered first, to remove as much of the tumor tissue as possible, and then one or more doses of the enhanced DC as described herein are administered. In another example, one or more doses of the enhanced DC as described herein are administered prior to administration of a dose of cytotoxic radiation or chemotherapy, e.g., to sensitize the tumor cells to the radiation or chemotherapy and thereby enhance the effect of the radiation or chemotherapy. See, e.g., Antonia et al., Clin. Cancer Res. 12(3):878-887 (2006); Schlom et al., Clin. Cancer Res. 13(13):3776-3781 (2007) Thus, the methods described herein can include first administering one or more doses of the enhanced DC as described herein, followed by one or more doses of radiation or chemotherapy.

Evaluating Subjects Pre-Treatment and Post-Treatment

Prior to initiation of the enhanced dendritic cell treatment, subjects can be tested for the need of treatment. The clinical signs and symptoms of cancer, which are known in the art, can be an indicator of treatment need although an earlier predictor of treatment is more desirable. The dose regimen of the enhanced dendritic cells can be adjusted based on the severity of clinical signs and symptoms of cancer.

Following administration of enhanced dendritic cells, the efficacy and safety of the treatment can be assessed in several ways, indirectly or directly. The parameters, including levels of biomarkers (for example, immune responses such as increased IFN-γ production), clinical signs and symptoms (for example, tumor response (e.g., growth and/or overall size) by imaging, progression-free survival or overall survival), and adverse events, can be evaluated over time in the same subject. The parameters can also be compared between actively treated subjects and placebo subjects at the same time points. The parameters can be the absolute values or the relative changes from the baseline in the same subject or compared to placebo subjects. The levels of biomarkers associated with cancer and treatment in subject samples can be monitored before and after treatment. The number and/or severity of clinical signs and symptoms in a subject can be compared before and after treatment, including long-term follow-up after the last dose. The adverse events can also be monitored and compared between active and placebo groups or between baseline and post-treatment in the active group. For example, a subject (e.g., a cancer patient) can have an initial assessment of the severity of his or her disorder (e.g., the number or severity of one or more symptoms of cancer), receive enhanced dendritic cell treatment as a monotherapy or part of a combination therapy, and then be assessed subsequently to the treatment at various time points (e.g., at one day, one week, one month, three months, six months, one year, two years and three years).

EXAMPLES

The present invention is further described in the following examples, which do not limit the scope of the invention described in the claims.

Example 1

Inefficient Trafficking of TP-DC to Lymph Nodes

Five to seven week old female C57BL/6 mice (denoted B6) were purchased from Harlan Laboratories (Indianapolis, Ind.). All mice were housed at least 1 week, and were age-matched before their usage in experiments.

The B16-BL6 (denoted B16) melanoma developed spontaneously in a B6 mouse and is poorly immunogenic (Fidler, Cancer Res 35:218 (1975)). B16 cells were cultured in complete medium (CM) (Kirk et al., Cancer Res 61:2062 (2001)) and maintained by serial in vitro passage.

To prepare B16 tumor lysate (TL), the cultured tumor cells were briefly trypsinized, washed extensively, counted, and re-suspended in PBS ($3 \times 10^7$ cells/ml). Four cycles of rapid freezing and thawing (5 minutes each) were performed in liquid nitrogen and a 37° C. water bath, respectively, followed by a 1 minute centrifugation at 500 rpm. The supernate was collected and used as TL for DC loading. Supernates were verified to be negative for endotoxin contamination by Pyrotell LAL test (detection limit, 0.03 EU/ml; Associates of Cape Cod, Inc., E. Falmouth, Mass.). To induce apoptotic cells, B16 was irradiated with 30,000 rad or treated with UVB light (302 nm) for 20 minutes (equal to 200 mJ/cm$^2$).

To prepare TL from freshly isolated B16 tumor, $1 \times 10^5$ B16 cells were injected subdermally into the flank of mice. Tumors were excised 3 weeks later, cleaned of capsule and necrotic areas, and disaggregated to single cells using an enzyme cocktail (Fields et al., Proc Natl Acad Sci USA 95:9482 (1998); Asavaroengchai et al., Proc Natl Acad Sci USA 99:931 (2002)).

The rat anti-mouse MARCO mAb (ED31) producing hybridoma was a gift from Dr. Kraal (Vrije Universiteit, Netherlands). ED31 is a rat IgG recognizing the ligand binding domain of MARCO (van der Laan et al., J Immunol 162:939 (1999)). ED31 was purified from supernates for further experiments (Ligocyte Pharmaceuticals, Inc., Bozeman, Mont.). Normal rat IgG (Sigma) was used as a negative control.

DC were generated from bone marrow cells (BMC) of B6 mice. BMC were flushed from the femurs and tibias of B6 mice under aseptic condition. Erythrocytes were lysed with ACK lysing buffer (0.15 M NH4Cl, 1 mM KHCO3, and 0.1 mM EDTA in sterile water). Erythrocyte-depleted BMC were washed twice with Dulbecco's phosphate-buffered saline (PBS) (Mediatech, Inc.) and suspended in CM containing 20 ng/ml of mouse granulocyte/macrophage colony-stimulating factor (GM-CSF) and 10 ng/ml of mouse interleukin-4 (IL-4) (both from R&D Systems, Minneapolis, Minn.) at the concentration $1 \times 10^6$ cells/ml, and then incubated at 37° C., 5% CO$_2$. At day 5, non-adherent cells were collected and DC were highly enriched (>95%) by density centrifugation over OptiPrep (Axis-Shield PoC AS, Oslo, Norway) (Fields et al., Proc Natl Acad Sci USA 95:9482 (1998); Asavaroengchai et al., Proc Natl Acad Sci USA 99:931 (2002)).

To load DC, tumor lysate (TL) was added in CM for 24 hours at a DC:TL ratio of 1:3 cell equivalents (Fields et al., Proc Natl Acad Sci USA 95:9482 (1998)). For treatment of DC with mAbs, 20 μg/ml anti-MARCO mAb or control rat IgG was added to CM containing TL during the 24 hour pulsing step. The treated, TP-DC were then washed twice with PBS and suspended in PBS for injection into mice. Viability of the DC after treatment with TL and mAbs was over 90% by trypan blue exclusion.

To stain B16 TL for microscopic or flow cytometric analyses of DC phagocytosis, PKH2 Green or PKH26 Red Fluorescent Cell Linker Kit (Sigma) was utilized according to the manufacturer's instruction. Trypsinized and washed B16 cells were first suspended in staining buffer. Staining was performed with $2 \times 10^{-6}$ M PKH2 dye ($1 \times 10^7$ cells/ml) for 5 minutes at room temperature. After staining, the cells were washed with CM once and with PBS thrice. TL of PKH2-stained B16 cells was made as described above.

An examination of the in vivo trafficking of TP-DC was conducted in mice using two-color confocal histo-microscopy of labeled TP-DC. The vast majority of TP-DC did not egress from a subdermal injection site, with only few localizing in the draining lymph node.

Example 2

Up-Regulation of MARCO Expression by DC

For detection of MARCO mRNA, DC were either left unpulsed, or pulsed with 1 µg/ml LPS (from E. coli 0111:B4; Sigma), B16 apoptotic cells, or B16 TL for 24 hours. To isolate mRNA from DC, RNeasy Micro Kit (Qiagen, Valencia, Calif.) was used according to supplier instructions.

For RT-PCR reactions, 100 ng mRNA was used to synthesize cDNA with Ready-to-Go RT-PCR beads (Amersham Biosciences, Buckinghamshire, England). The cDNA synthesis reaction was performed at 37° C. for 60 minutes followed by 95° C. for 5 minutes. After the cDNA reaction, 400 nM primers were added into the reaction mixture. The following primers were used for murine MARCO PCR reactions; Sense: 5'-GCA CTG CTG CTG ATT CAA GTT C-3' (SEQ ID NO:1), Anti-sense: 5'-AGT TGC TCC TGG CTG GTA TG-3' (SEQ ID NO:2) (205 bp product). To detect MARCO expression in human cells, the following primers were used: Sense 5'-AAA TCA ATG TTC CAA AGC CCA AGA A-3' (SEQ ID NO:3), Anti-sense: 5'-CCT GTT GCT CCA TCT CGT CCC ATA G-3' (SEQ ID NO:4) (481 bp product). For GAPDH reactions, PCR primer pairs (mouse/rat GAPDH or human GAPDH: R&D Systems) were used. PCR amplification conditions were as follows: denaturation at 94° C. for 5 minutes, amplification composed of denaturation at 94° C. for 30 sec, annealing at 57° C. for 30 sec, and extension at 72° C. for 1 minute, followed by a final extension at 72° C. for 10 minutes. Amplification was performed using thirty-five cycles. Amplification products were separated on a 1% agarose gel, counter-stained with ethidium bromide, and viewed with Gel-Doc 200 (Biorad).

Figure 2:
FIG. 2 is an image of a gel showing MARCO mRNA expression by DC loaded with different forms of killed B16 melanoma cells. Lanes 1-5: MARCO mRNA; lanes 6-10: GAPDH. Lanes 1 and 6: unpulsed DC; lanes 2 and 7: LPS-pulsed DC; lanes 3 and 8: B16 TL-loaded DC; lanes 4 and 9: B16 UV intact-loaded DC; lanes 5 and 10: B16 irradiated intact-loaded DC.

Murine bone marrow-derived DC were left unpulsed or exposed to 1 µg/ml LPS or B16 melanoma lysate. Twenty-four hours later, mRNA was extracted and MARCO expression was analyzed by RT-PCR (FIG. 1). Both LPS- and TP-DC showed up-regulated MARCO expression. Up-regulation of MARCO mRNA expression in DC could also be detected following their exposure to either UV-treated or irradiated, intact B16 melanoma cells (FIG. 2).

Human DC were generated from peripheral blood mononuclear cells of normal volunteers, as described previously (Chang et al., Clin Cancer Res 8:1021 (2002); Geiger et al., Cancer Res 61:8513 (2001)). Briefly, PBMCs were recovered from leukapheresis product by density gradient centrifugation over Accu-Prep Lymphocytes (Accurate Chemical & Scientific Corp., Westbury, N.Y.). The PBMCs were resuspended in X-VIVO 15 medium (BioWhittaker) at $1 \times 10^7$ cells/ml, and 30 ml of cell suspension were added to each 225-$cm^2$ tissue culture flask (Costar). The flasks were incubated in 5% $CO_2$ at 37° C., and after 2 hours, the nonadherent cells were gently removed. The adherent cells were cultured in X-VIVO 15 medium containing recombinant human granulocyte/monocyte colony-stimulating factor (100 ug/ml; Schering-Plough, Kenilworth, N.J.) and recombinant human IL-4 (50 ug/ml; Schering-Plough) for 6 days. After 6 days, the DCs were harvested by adding 10 ml of 3 mM EDTA-PBS. A total of $1 \times 10^7$ DC was transferred to 75-cm2 flasks (Costar) and either pulsed at a 1:1 ratio with autologous tumor lysates or 300 ul of KLH stock solution (50 ug/ml; Calbiochem, San Diego, Calif.).

Figure 3:
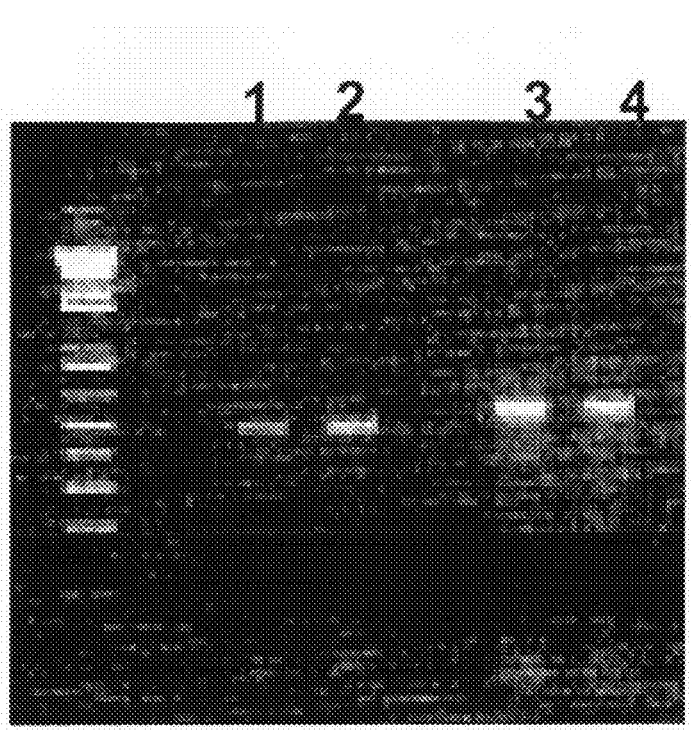
FIG. 3 is an image of a gel showing human MARCO transcript (481 bp product) expression by human lymph node cells (lane 1) and human 5-day monocyte-derived DC (lane 2). Lanes 3 and 4 contain the GAPDH controls.

Human monocyte-derived DC were examined by RT-PCR for the presence of the MARCO transcript (a 481 bp PCR product) as well. MARCO was expressed by both human lymph node cells and human DC (lanes 1 and 2, respectively; FIG. 3).

For immunofluorescence microscopy, fluorescein isothiocyanate (FITC)-conjugated anti-CD11c mAb and appropriate isotype-matched control (BD Biosciences) were employed for DC staining.

For cell surface staining, cells were washed with flow buffer (0.01% $NaN_3$, 2% fetal bovine serum in PBS) and Fcγ III/II receptor blocking was performed by purified anti-mouse CD16/32 (BD Biosciences). The blocking mAb (1 µg/$1 \times 10^6$ cells) was added to cells on ice for 10 minutes. Additional mAbs (1 µg/$1 \times 10^6$ cells) for cell surface staining were then added on ice for an additional 30 minutes protected from light. After washing twice with flow buffer, the stained cells were fixed with 1% paraformaldehyde (PFA) in PBS. Data acquisition and analyses were performed by a FACScan flow cytometer and CellQuest software (BD Biosciences), respectively.

TP-DC were washed with flow buffer and stained with rat anti-MARCO mAb or rat IgG1 as a negative control (Serotec) followed by the staining with Alexa Fluor 594 chicken anti-rat IgG and Alexa Fluor 488 hamster anti-mouse CD11c (both from Invitrogen Corp.).

After the staining procedure, TP-DC were washed twice with PBS and fixed with 1% PFA for 1 hour at room temperature. To examine MARCO expression by DC pulsed with labeled TL, DC was first cultured with PKH2 green or PKH26 red-stained B16 TL for 24 hr. After the incubation, the DC were washed twice with PBS, stained with anti-MARCO mAb followed by Alexa Fluor 488 or Alexa Fluor 594 chicken anti-rat IgG, fixed with 1% PFA, and spun onto glass slides by a Shandon Cytospin-2 (International Medical Equipment, Inc., San Marcos, Calif.) at 800 rpm for 5 minutes. The slides were then mounted with Gel/Mount (Biomeda Corp. Foster City, Calif.) for anti-fading. Alternatively, slides were mounted with Vectashield mounting medium containing DAPI according to the manufacturer's instructions (Vector Laboratories, Inc., Burlingame, Calif.). Slides were viewed with a fully automated, upright Zeiss Axio-ImagerZ.1 microscope (Carl Zeiss MicroImaging, Inc., Thornwood, N.Y.). Images were produced using the AxioCam MRm CCD camera and Axiovision version 4.5 software suite (Carl Zeiss MicroImaging, Inc.).

To visualize cell surface expression of MARCO, TP-DC were first stained with fluorescent-labeled anti-MARCO and anti-CD11c mAbs. Many, but not all, of the CD11c+TP-DC co-exhibited MARCO expression (i.e. 67%-82% over a 72 hour period of B16 melanoma lysate loading), which appeared as a uniform surface distribution pattern. The expression of MARCO on the cell surface of B16 tumor lysate-captured DC was the directly examined. In this case, DC were co-cultured with PKH2 Green- or PKH26 Red-stained B16 TL for 24 hours before labeling with anti-MARCO mAb. These studies confirmed that MARCO was indeed expressed on the surface of TP-DC (as opposed to internally) and thus could be easily targeted by anti-MARCO antibodies to produce enhanced dendritic cells.

Example 3

Functional Assessment of MARCO Expressed by DC

The effects of exposure to anti-MARCO mAb on certain DC biologic properties were examined.

DC were cultured with different concentrations of anti-MARCO or anti-CD80 mAb together with B16 TL in Lab-Tek II Chamber Slide System (Nalge Nunc International Corp, Naperville Ill.). After overnight culture, TP-DC were stained with Wright's and morphologic observation was performed under the light microscope.

Figure 4:
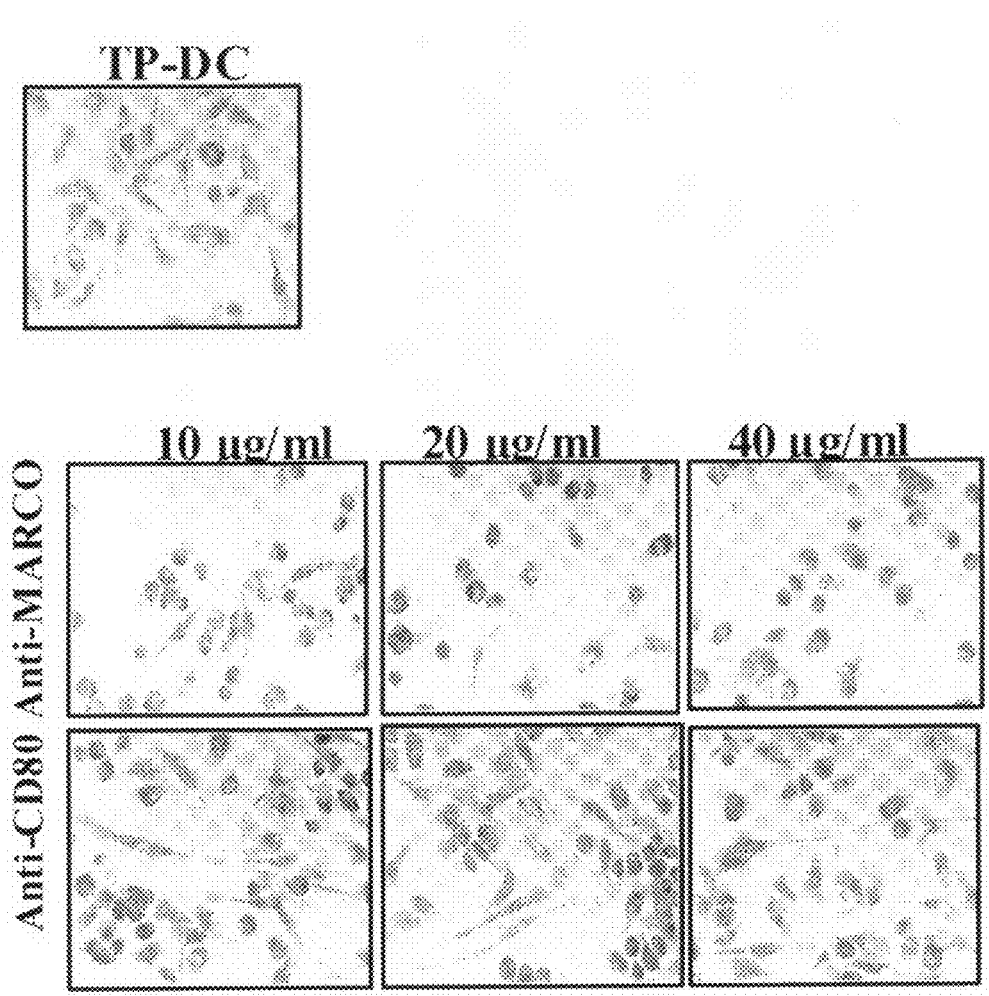
FIG. 4 is a set of seven light microscopy images of anti-MARCO mAb-treated TP-DCs. Exposure of B16 melanoma lysate-loaded DC (top row) to anti-MARCO mAb in vitro leads to cell rounding and loss of dendritic processes (middle row). Such morphologic changes were not observed following incubation of the DC to antibody directed toward a second cell surface expressed molecule, CD80 (bottom row). Representative of two separate experiments.

Overnight exposure of DC to various concentrations of anti-MARCO mAb (10, 20 and 40 μg/ml) together with B16 melanoma lysate resulted in a rounded morphology with loss of membrane dendritic processes (FIG. 4, middle row), compared to untreated TP-DC (FIG. 4, top row); the DC remained highly viable. The change in morphology was not observed when the DC were similarly treated with control rat IgG (not shown) or anti-CD80 mAb directed to a second, cell surface expressed molecule (FIG. 4, lower row).

Phagocytic activity of DC upon treatment with anti-MARCO mAb was also examined. DC were co-cultured at 37° C. with PKH2-stained (PKH2 Green Fluorescent Cell Linker Kit; Sigma) B16 TL for 24 hours together with control rat IgG or anti-MARCO mAb. For a negative control, DC were co-cultured with stained B16 TL at 4° C. To compare phagocytic activity of anti-MARCO mAb-treated DC with matured DC, DC were exposed to LPS during the culture period with stained B16 TL. After 24 hours in culture, DC were stained with PE-conjugated anti-CD11c and the percentage of double positive CD11c/PKH2 cells were assessed by flow cytometry.

Figure 5:
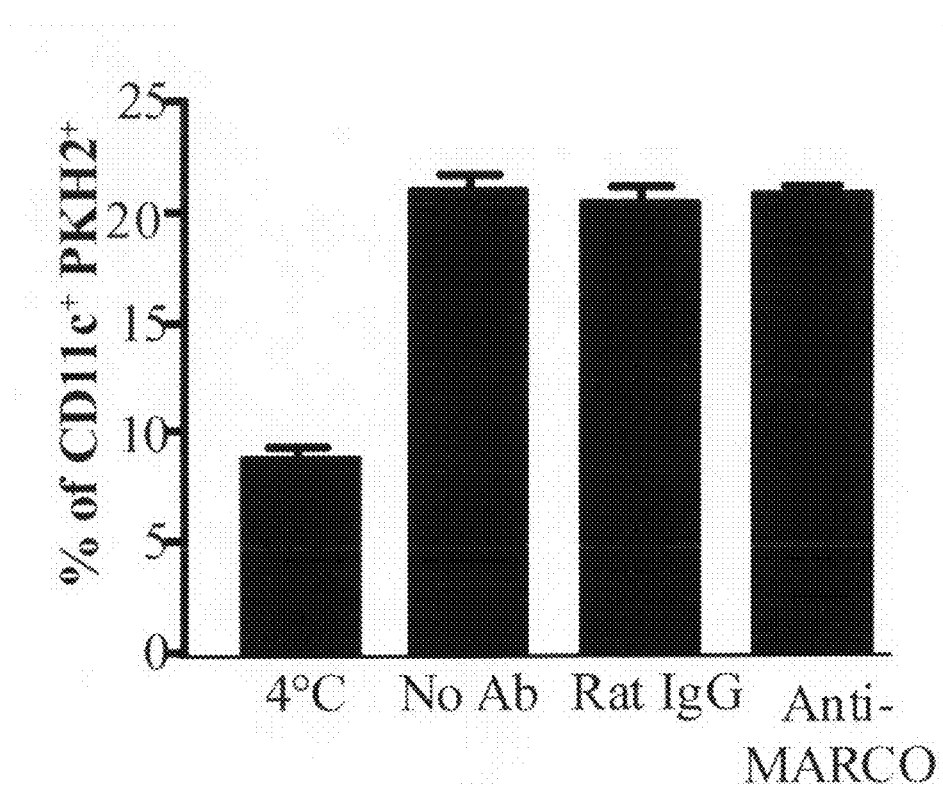
FIG. 5 is a bar graph illustrating the results of flow cytometry of phagocytic activity of anti-MARCO mAb-treated DC. Pre-treatment of DC with anti-MARCO mAb (20 μg/ml) does not affect uptake of B16 melanoma lysate in an in vitro phagocytosis assay. DC were stained with PE-conjugated anti-CD11 and the percentage of double positive CD11c/PKH2 cells were assessed by flow cytometry.
Figure 6A:
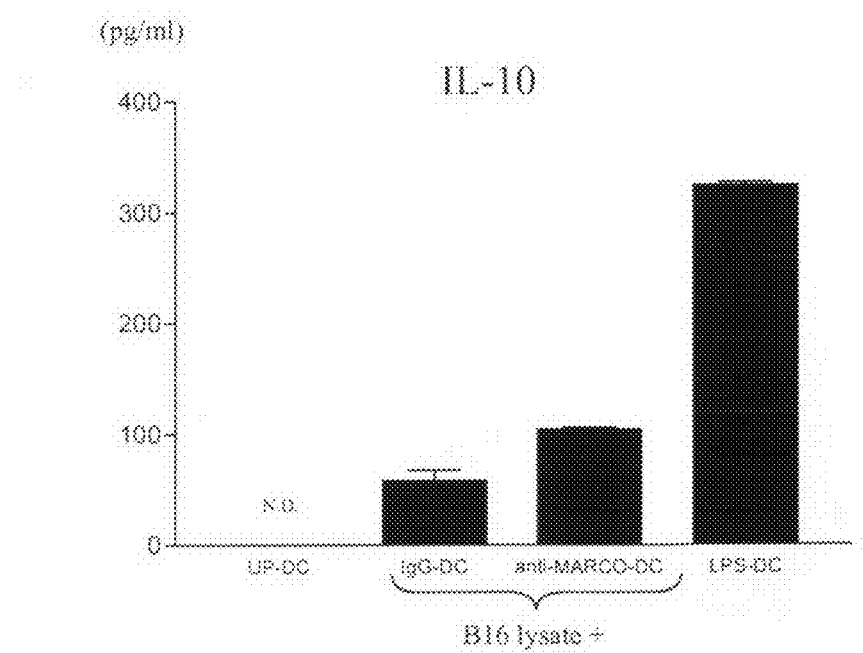
FIGS. 6A-6C are bar graphs showing cytokine (IL-10 (6A), IL-12p70 (6B), and TNF-α (6C)) production by anti-MARCO mAb-treated TP-DC. Supernates were collected 24 hours after incubation and cytokines were measured by ELISA.
Figure 6B:
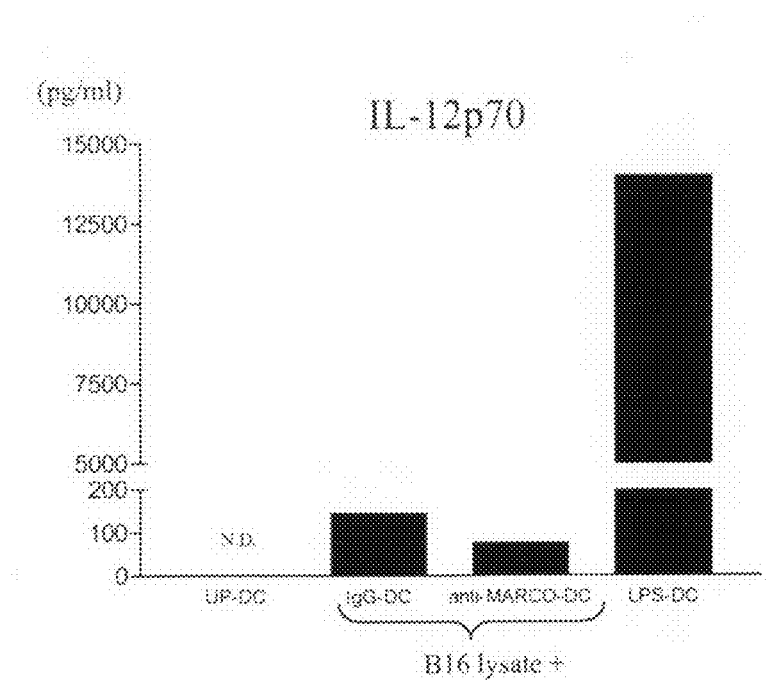
Figure 6C:
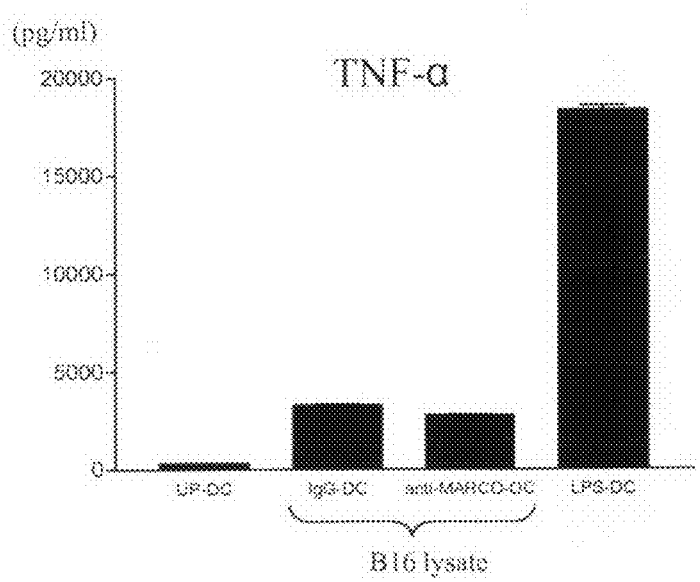

As shown in FIG. 5, anti-MARCO mAb treatment of unpulsed DC (i.e. targeting the "steady state" level MARCO surface expression) did not adversely impact subsequent uptake of B16 TL (% CD11c+PKH2+ cells (mean±SD): no Ab, 20.9±1.2; rat IgG, 20.4±1.2; anti-MARCO mAb, 20.8±0.5). Similarly, little, if any, change was detected in TP-DC production of IL-10, IL-12p70 and TNF-alpha cytokines following anti-MARCO mAb treatment (FIG. 6).

Microchemotaxis assays were then performed to assess the effect of anti-MARCO mAb on chemotactic activity of DC in vitro in a 24-well plate format with 6.5-mm diameter, 5 μm pore polycarbonate Transwell insets (Coster, Cambridge, Mass.). DC were left unpulsed or pulsed with B16 TL and control rat IgG, B16 TL and anti-MARCO mAb, or 1 μg/ml LPS for 24 hr. DC were then washed twice with PBS and suspended in pre-warmed CM at $3 \times 10^6$ cells/ml. Before the assay, 600 μl of CM containing 100 ng/ml murine Exodus-2 (SLC: PeproTech. Inc., Rocky Hill, N.J.) was placed into the lower chamber and the plate was incubated at 37° C. for 30 minutes. DC ($3 \times 10^5$) were then placed into the upper chamber and the assay was carried out at 37° C. in a humidified incubator with 5% $CO_2$. After 6 hr, the upper chamber was removed. Polystyrene beads (15 μm diameter, Bangs Laboratories, Inc., Fishers, Ind.) were used to count migrated DC by flow cytometry. DC in the lower chamber were stained with I-Ab and CD11c mAbs and the double positive cells were enumerated. The migrating samples were compared with input samples that did not involve microchemotaxis and is presented as the percentage of input migrating DC.

Figure 7:
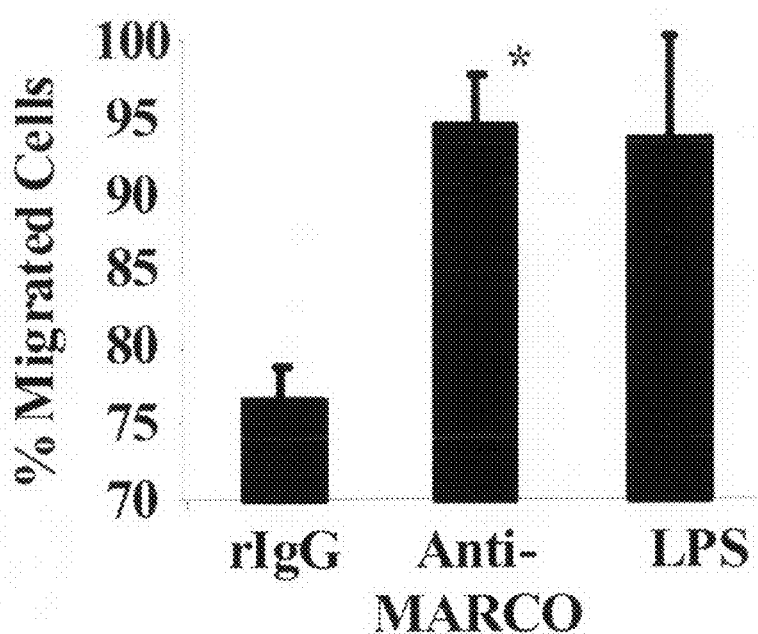
FIG. 7 is a bar graph showing the chemotactic response of B16 melanoma lysate-loaded DC to CCL-21 in vitro. Exposure of these DC to anti-MARCO mAb enhanced chemotaxis similar to treatment with LPS. *, P<0.05 for anti-MARCO mAb and LPS vs. control IgG by Student's t test. Bars, SEM. Representative of three separate experiments.

SLC/CCL-21 is a potent chemoattractant of DC in vitro and in vivo (Kirk et al., Cancer Res 61:2062 (2001)). TP-DC treated with anti-MARCO mAb (i.e. enhanced dendritic cells) showed improved migration to SLC/CCL-21 as measured by the number of CD11c+I-Ab+cells appearing in the lower chamber [% migrating cells (mean±SD): control rat IgG, 76.4±2.4; anti-MARCO mAb, 94.5±3.3, *p<0.05], which was similar to LPS-treated TP-DC (93.8±7.3) (FIG. 7).

Example 4

Targeting MARCO Enhances Both DC Migration to Lymph Node and Anti-Tumor Efficacy In Vivo Whether targeting MARCO would impact on the migration of TP-DC into lymph nodes after subdermal injection was examined in vivo. DC were pulsed with either B16 TL and control rat IgG or B16 TL and anti-MARCO mAb for 24 hours and then washed twice with PBS. These TP-DC were stained with $2 \times 10^{-6}$ M PKH26 dye (PKH26 Red Fluorescent Cell Linker Kit; Sigma) at $1 \times 10^7$ cells/ml for 5 minutes at room temperature, then washed with CM once and with PBS three times. TP-DC viability was over 90%. The PKH26-stained TP-DC were then suspended in PBS and $5 \times 10^6$ cells/100 μl (or PBS alone) were injected subdermally into the rear flanks of B6 mice (n=4). Inguinal lymph nodes were collected 48 hours later and fixed in 3.7% formaldehyde solution at room temperature. The samples were plated onto dishes for microscopic examination and migrated TP-DC were observed by a Zeiss LSM 510 confocal microscope (Carl Zeiss MicroImaging, Inc.). Images were produced with the LSM 5 version 3,2,0115 software suite (Carl Zeiss MicroImaging, Inc.).

Anti-MARCO mAb-treated TP-DC (i.e. enhanced dendritic cells) demonstrated heightened lymph node accumulation. Of note, these enhanced dendritic cells could also be detected to some extent in the spleen compared to control rat IgG treated DC.

Because enhanced migration of TP-DC to lymph nodes could be achieved by anti-MARCO mAb treatment (i.e. enhanced dendritic cells), its impact on vaccine efficacy against established B16 melanoma was investigated. B6 mice received $1 \times 10^5$ B16 melanoma cells subdermally in the right flank. DC were pulsed with B16 TL and treated with 20 μg/ml control rat IgG or anti-MARCO mAb for 24 hr. Mice received $1 \times 10^6$ TP-DC (or PBS alone) in the left flank subdermally, 3, 6 and 9 days after the tumor injection.

One-way ANOVA and Student's t-test were performed for comparisons of groups and to compare between two groups, respectively. All statistical evaluations employed GraphPad Prism (GraphPad Software, Inc., San Diego, Calif.). Statistical significance was achieved at p<0.05.

Table 1 shows the results of 3 combined experiments. In this treatment model, control rat IgG-treated TP-DC did not show an anti-tumor effect [mean±SD tumor area (mm$^2$) at day 25: PBS, 321.63±40.53; control rat IgG-DC, 298.55±38.90]. In contrast, the injection of anti-MARCO mAb-treated TP-DC (i.e. enhanced dendritic cells) resulted in an approximate 50% tumor growth inhibition (167.74±32.82, **p<0.01).

TABLE 1

Enhanced anti-tumor efficacy in vivo following treatment with TP-DC exposed to anti-MARCO mAb (i.e. enhanced dendritic cells)

| Treatment | Day 12 | Day 20 | Day 25 |
|---|---|---|---|
| PBS | 29.82 ± 5.77a | 170.17 ± 28.77 | 321.63 ± 40.53 |
| Control Rat IgG-DC | 32.72 ± 6.07b | 164.43 ± 25.99 | 298.55 ± 38.90 |
| Anti-MARCO-DC | 20.53 ± 4.35 | 81.01 ± 14.45 | 167.74 ± 32.82 |

Mice received $1 \times 10^5$ viable B16 melanoma cells subdermally in the right flank. DC were loaded with B16 TL and treated with 20 μg/ml control rat IgG or anti-MARCO mAb. Mice received $1 \times 10^6$ TP-DC (or PBS alone) subdermally in the left flank 3, 6 and 9 days after tumor injection.
Data are shown as mean ± SD tumor area (mm$^2$) and are a compendium of three separate experiments combined.
* p < 0.01 vs. control rat IgG-DC or PBS.
** p < 0.02 vs. control rat IgG; p < 0.01 vs. PBS.

Example 5

Targeting MARCO on TP-DC Enhances Anti-Tumor T Cell Reactivity

To examine the induction of cellular immune response following anti-MARCO mAb-treated TP-DC (i.e. enhanced dendritic cells) injection, both IFN-γ production and T cell proliferation were measured in immunized mice.

B6 mice were immunized subdermally thrice, 3 days apart with the $1\times10^6$ DC pulsed with B16 TL and treated with control rat IgG or anti-MARCO mAb. Six days after final vaccination, spleens were removed under aseptic condition and erythrocyte-depleted lymphocytes were prepared from gently teased apart spleens. T cells in the lymphocytes were isolated with Mouse T-Cell Enrichment Column Kit (R&D Systems). After the isolation, T cells were suspended in CM at the concentration $1\times10^6$ cells/ml and cultured with or without TP-DC for 48 hr. The concentration of T cell:TP-DC for the culture was 10:1. After 48 hours of incubation, supernates were collected and IFN-γ was measured with a murine IFN-γ ELISA set (BD Biosciences).

A $^3$H-thymidine incorporation assay was performed to examine B16 melanoma-specific lymphocyte proliferation. Mice were immunized thrice, 3 days apart, with $1\times10^6$ DC pretreated with B16 TL and control rat IgG or anti-MARCO mAb. Seven days after final vaccination, spleens were removed and erythrocytes-depleted lymphocytes were prepared. The splenocytes were suspended in CM at the concentration $1\times10^6$ cells/ml. The cells were plated into 96-well, round bottom plates (Corning Incorporated, Corning, N.Y.) in 100 μl volumes and incubated in a final volume of 200 μl with CM alone or irradiated (1,500 rad) TP-DC at splenocyte:TP-DC of 100:1. For the control, $1\times10^3$ irradiated TP-DC were plated in the wells. The cells were co-cultured at 37° C., 5% $CO_2$ for 3 days. The cultures were pulsed overnight with 1 μCi/well of $^3$H-thymidine (PekinElmer, Boston, Mass.). Harvest was performed by a FilterMate Harvester (PerkinElmer) onto Filtermat A glass-fiber filter (PerkinElmer) and data were collected by a 1450 MicroBeta TriLux scintillation counter (PerkinElmer).

Figure 8A:
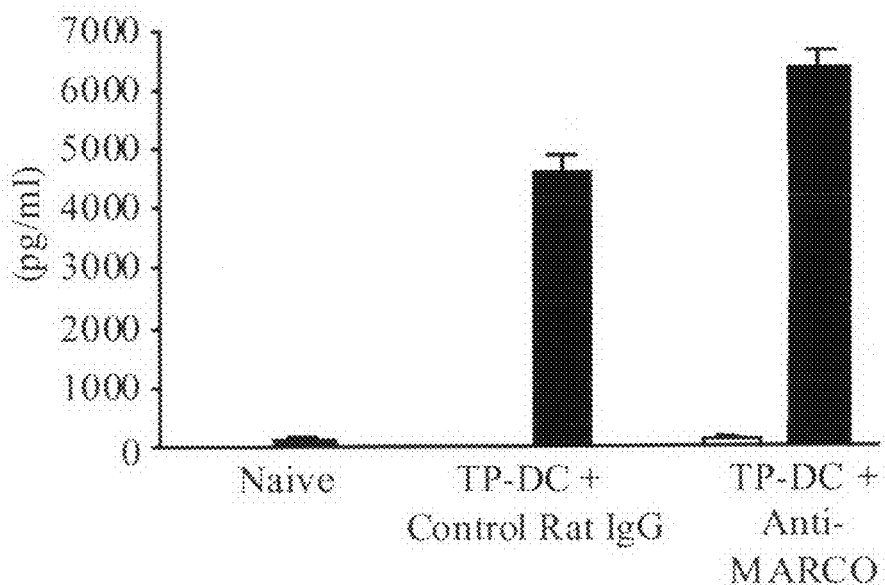
FIGS. 8A and 8B are bar graphs showing the enhancement of (8A) IFN-γ production and (8B) splenic T cell proliferation by immunization with anti-MARCO mAb-treated TP-DC. Naïve or TP-DC immunized mice served as splenic T cell donors. The T cells were restimulated in vitro.
Figure 8B:
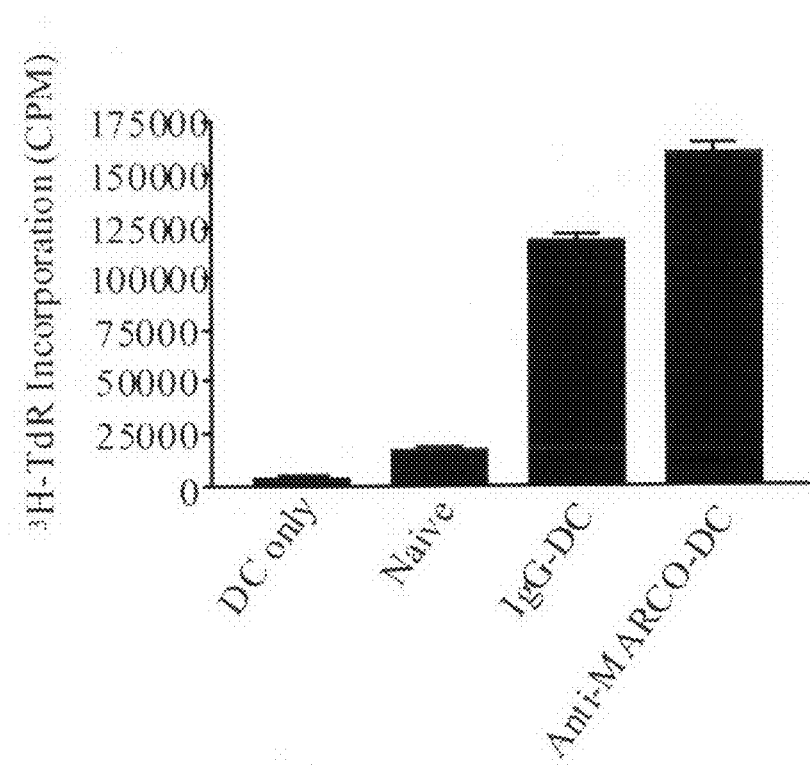

As shown in FIG. 8A, T cells from mice immunized with anti-MARCO mAb-treated TP-DC (i.e. enhanced dendritic cells) produced a greater amount of IFN-γ compared to those from control rat IgG treated TP-DC immunized mice (6,333±705 pg/ml vs. 4,561±843 pg/ml, respectively, *p<0.01). Similarly, as shown in FIG. 8B, spleen cells from mice immunized with anti-MARCO mAb-treated TP-DC (i.e. enhanced dendritic cells) also showed a stronger anti-tumor proliferative response (mean cpm±SD: 161,168±7,231 vs. 116,526±7,243 for control rat IgG TP-DC immunized mice, *p<0.005).

Collectively, the findings reported herein demonstrate that targeting MARCO expression can enhance both the trafficking and anti-tumor efficacy of TP-DC.

As one theory, not meant to be limiting the enhanced arrival of TP-DC at peripheral lymphoid tissues achieved by targeting MARCO (i.e. enhanced dendritic cells) may be responsible for the enhanced anti-tumor T cell reactivity detected. This correlation is supported by the findings that TP-DC treated with anti-MARCO mAb (i.e. enhanced dendritic cells) or control IgG have the same levels of antigen presentation capacity (peptides or whole protein) to TCR transgenic T cells in vitro (data not shown) and produce similar levels of cytokines in vitro (FIG. 6). The improved in vitro migration of TP-DC by anti-MARCO mAb exposure (i.e. enhanced dendritic cells), as measured in microchemotaxis assays, was a general phenomenon and not due to the presence of SLC/CCL-21 per se, as similar behavior was observed in CM alone and a change in the level of CCR7 by TP-DC was not detected (data not shown). This finding also correlates with the morphologic shape change (i.e., rounding with loss of dendritic processes) of TP-DC following anti-MARCO mAb exposure (i.e. enhanced dendritic cells). In this regard, MARCO expression has been shown to be sufficient to induce actin cytoskeleton rearrangement (Granucci et al., Blood 102:2940 (2003)) and the change in morphology observed with anti-MARCO mAb-treated TP-DC (i.e. enhanced dendritic cells) may also play a participatory role in the increased migratory behavior observed in the microchemotaxis assay as well as in vivo.

Example 6

Methods of Preparing Enhanced Human Dendritic Cells

This Example describes exemplary methods for preparing a population of enhanced human dendritic cells, suitable for use in the methods of treatment described herein.

Tumor Lysate

Tumors are harvested surgically for palliative or curative intent. The harvested tumors can be used freshly or cryopreserved for later use. Tumors are kept sterile on ice and transported from the operating room to the laboratory. A single cell suspension is made by a combination of mechanical and enzyme dispersion techniques. Chemical digestion is completed by incubation in 50-ml RPMI (BioWhittaker, Walkersville, Md.), 0.00044% DNase I (Sigma Chemical Co., St. Louis Mo.), 150 units/ml collagenase (Sigma Chemical Co.), and 750 units/ml hyaluronidase (Sigma Chemical Co.) with constant stirring for 3-12 hours. The resulting cell suspension is passed through a 70-μm cell strainer. The flow-through is pelleted, resuspended in DMEM (Life Technologies, Inc., Grand Island, N.Y.)/10% heat-inactivated fetal bovine serum (BioWhittaker)/1×Transferrin-Insulin-Selenium A (Life Technologies, Inc.), and cultured in a tissue culture flask at 37° C., 5% $CO_2$. Trypsin-EDTA (Life Technologies, Inc.) is used to passage tumor cell lines. For long-term storage, tumor cells are frozen in 90% human AB serum (BioWhittaker) and 10% DMSO in a liquid nitrogen freezer.

Tumor cells (fresh or short-term cultured cell lines) are suspended in PBS. The cell suspension is frozen in liquid nitrogen for 1.5 minutes, then thawed in a 37° C. water bath for 4 minutes. The freeze-thaw cycle is repeated three times in rapid succession; cells are irradiated at 10,000 cGy and stored in liquid nitrogen for later use (Chang et al., Clin Cancer Res 8:1021 (2002); Geiger et al., Cancer Res 61:8513 (2001)).

Enhanced Dendritic Cells

Subjects undergo a 4-hour leukapheresis on a COBE spectrum apheresis system to ensure adequate numbers of peripheral blood mononuclear cells (PBMCs) for dendritic cell culture and for immune monitoring. PBMCs are obtained by taking the apheresis product, diluting it 4-fold in HBSS (Life Technologies, Inc., Grand Island, N.Y.), and overlaying it on Ficoll-Hypaque gradients. The cells are then centrifuged at 900×g for 30 minutes at room temperature. The interface representing the PBMCs are then collected and washed in HBSS twice to reduce platelets. Aliquots of PBMCs are then cryopreserved in 70% human AB serum 20% X-VIVO 15 and 10% DMSO for future use in cryopreservation bags (Baxter Corp., Deerfield, Ill.) or cryovials.

In very young subjects, special procedure may be required. Children with less than 20 kg body weight may require a blood prime to maintain hemodynamic stability; for these subjects, a WBC set on the COBE spectrum apheresis system is used to perform a manual cell collection. Children with greater than 20 kg body weight can tolerate the procedural fluid shifts, and, therefore, automated cell collection is performed. Flow rates are determined by the child's size as the machine has an extensive algorithm to determine anticoagulant tolerance. The process of two to three times the subject's blood volume averaged 3-4 hour/procedure. Venous access is accomplished by either two large peripheral arm veins, if the subject is cooperative, or, as in most cases, by a rigid dialysis catheter placed in the femoral vein and then removed post leukapheresis. Product volumes vary depending on the type of collection performed. WBC/manual collection yields a product of about 100-250 ml, whereas auto PBSC is more concentrated yielding 40-100 ml. Subject's ionized calcium level is routinely measured and titrated a calcium gluconate drip to maintain the ionized calcium at 1-1.3 mM.

Dendritic cells are prepared from the fresh leukapheresis sample or cryopreserved PBMCs obtained from the pretreatment leukapheresis. PBMCs are resuspended in serum-free X-VIVO 15 medium (BioWhittaker, Walkerville, Md.) at $1 \times 10^7$ cells/ml for a total volume of 30 ml in 225-cm² flasks. The cells are allowed to adhere for 2 hours at 37° C. in 5% $CO_2$, and the nonadherent cells are removed after gentle rocking of the flasks and aspiration of the medium. Immediate replacement of 30 ml of X-VIVO 15 medium containing GM-CSF (100 μg/ml, Schering-Plough, Kenilworth, N.J.) and IL-4 (50 μg/ml; Schering-Plough) is completed, and the cells are incubated for 6 days at 37° C., 5% $CO_2$ before pulsing with tumor lysate and anti-MARCO antibody (Chang et al., Clin Cancer Res 8:1021 (2002); Geiger et al., Cancer Res 61:8513 (2001)).

The adherent dendritic cells are harvested from the flasks using 10 ml of EDTA (3 mM) for each flask and allowed to incubate for 10 minutes. The detached dendritic cells are harvested, washed, and resuspended at $1 \times 10^6$ cells/ml in fresh X-VIVO 15 medium containing GM-CSF and IL-4. Ten ml of the cell suspension are placed in 75-cm² flasks ($10^7$ dendritic cells/flask) for pulsing with tumor lysate and anti-MARCO antibody. Tumor lysate suspension is added to dendritic cell suspension at 1:1 cell equivalent ratio. Specifically, a volume of tumor lysate equal to $10^7$ tumor cells is added to each flask. Anti-MARCO antibody (20 μg/mL) is also added to the suspension. The cell suspension is incubated for 18 hours at 37° C., 5% $CO_2$.

After incubation, the tumor lysate-pulsed and anti-MARCO antibody-treated dendritic cells (i.e., enhanced dendritic cells) are harvested and counted. The enhanced dendritic cell suspension is adjusted to a total volume of 0.5 ml of PBS. For the dose level of $10^8$ enhanced dendritic cells, the cell suspension is divided into five separate syringes each containing 0.5 ml for intradermal administration.

Example 7

Figure 9:
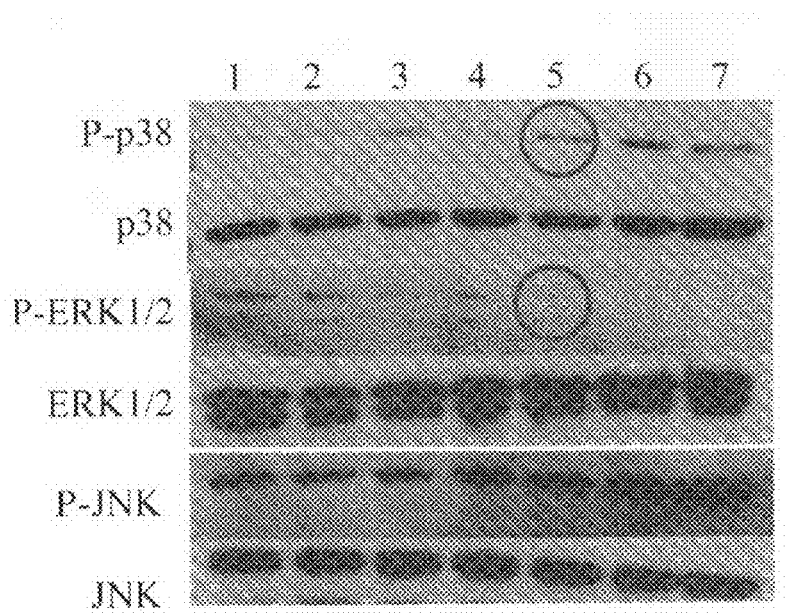
FIG. 9 is a Western Blot showing the results of analysis of levels of phosphorylated and total p38, ERK 1/2, and JNK. Lane 1: unpulsed DC; Lane 2: rIgG 20 ug/ml pulsed DC; Lane 3: ED31 20 ug/ml pulsed DC; Lane 4: rIgG 20 ug/ml+B16 lysate pulsed DC; Lane 5: ED31 20 ug/ml+B16 lysate pulsed DC; Lane 6: rIgG 20 ug/ml+LPS 1 ug/ml pulsed DC; Lane 7: ED31 20 ug/ml+LPS 1 ug/ml pulsed DC. P38 signaling was increased, ERK 1/2 signaling was decreased, and JNK signalling was substantially unchanged by treatment with the anti-MARCO antibody.

Anti-MARCO Antibodies Increase p38 Signalling, and Decrease ERK Signaling, in DC To determine whether the anti-MARCO antibody was affecting signal transduction pathways in DC. As shown in FIG. 9, wild type mouse bone-marrow derived DC were untreated (lane 1) or treated for 6 hours with rIgG 20 ug/ml (lane 2); ED31 at 20 ug/ml (lane 3); rIgG at 20 ug/ml+B16 lysate (lane 4); ED31 at 20 ug/ml+B16 lysate (lane 5) rIgG at 20 ug/ml+LPS 1 ug/ml (lane 6); or ED31 at 20 ug/ml+LPS 1 ug/ml (lane 7). Cells were collected and lysates were made using standard methods; Western blotting using phosphoprotein specific antibodies was then performed to detect levels of phosphorylated and total p38 (top two rows); phosphorylated and total ERK 1/2 (third and fourth rows); and phosphorylated and total JNK (bottom two rows). In this case, the presence of increased levels of the phosphorylated form of the protein is an indication that the pathway is activated. LPS pulsed DC were used as a positive control. LPS treatment increased P38 and decreased ERK signaling in the DC. Interestingly, ED31 treated DC increased P38 and decreased ERK. The results showed that the anti-MARCO antibody ED31 enhances P38 and decreases ERK signaling in these cells. As one hypothesis, ED31 treatment may lead to maturation of the tumor lysate-pulsed DC.

Figure 10:
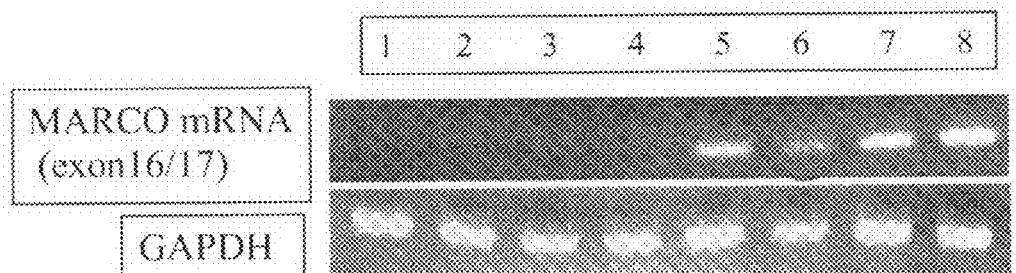
FIG. 10 is a blot showing the results of RT-PCR analysis of MARCO transcript levels in unpulsed DCs (lanes 1-4) and LPS-pulsed DC (lanes 5 to 8) with inhibitors of p38 (lanes 2 and 6), ERK (lanes 3 and 7), or JNK (lanes 4 and 8). The p38 inhibitor decreased MARCO expression.

Further experiments were conducted to determine whether the ED31 anti-MARCO antibody increased MARCO expression in the DC. ED31 treatment of TP-DC was compared to treatment with an IgG control, and MARCO expression was determined using standard RT-PCR with MARCO-specific primers. The DC were co-cultured with each inhibitor for 6 hours. The results, shown in FIG. 10, demonstrated that ED31 treatment increased MARCO expression in TP-DC, as compared to the IgG control. RT-PCR analysis of MARCO transcript levels was performed in unpulsed DC (lanes 1-4) and LPS-pulsed DC (lanes 5 to 8) with inhibitors of p38 (lanes 2 and 6), ERK (lanes 3 and 7), or JNK (lanes 4 and 8). The p38 inhibitor decreased MARCO expression, suggesting that MARCO expression in DC may be regulated via the p38 MAP kinase pathway.

Figure 11:
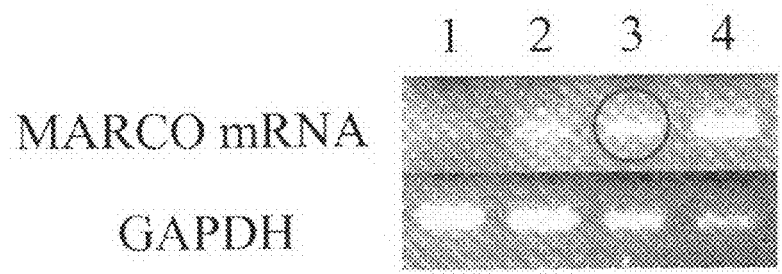
FIG. 11 is a blot showing the results of RT-PCT analysis of MARCO transcript levels in unpulsed DCs (lane 1), rIgG 20 ug/ml+B16 tumor lysate pulsed DC (lane 2); ED31 20 ug/ml+ B16 tumor lysate pulsed DC (lane 3); and LPS 1 ug/ml pulsed DC (lane 4). MARCO expression was increased in ED31 plus tumor lysate pulsed DC compared to IgG control added lysate pulsed DC.

Finally, the effect of a P38 inhibitor on MARCO expression was evaluated. RT-PCR was performed on DC pulsed with B16 tumor lysate (i.e. TP-DC) and ED31 or rat IgG control (rIgG) for 6 hours. The results, shown in FIG. 11, demonstrated that ED31 treatment increased MARCO expression in TP-DC, as compared to an IgG control.

These results indicated that ED31 treatment stimulated the p38 MAPK pathway and increased MARCO expression in TP-DC.

Other Embodiments

It is to be understood that while the technology has been described in conjunction with the detailed description thereof, the foregoing description is intended to illustrate and not limit the scope of the technology, which is defined by the scope of the appended claims. Other aspects, advantages, and modifications are within the scope of the following claims.

What is claimed is:

1. A method of treating a cancer in a subject, the method comprising:
    obtaining an initial enriched population of dendritic cells from the subject;
    contacting the initial enriched population of dendritic cells with:
        dead tumor cells; and
        an antibody or antigen-binding fragment thereof that binds to macrophage receptor with collagenous structure (MARCO), thereby preparing a population of enhanced dendritic cells; and
    administering to the subject a therapeutically effective amount of the enhanced dendritic cells, thereby treating the cancer in the subject.

2. The method of claim 1, wherein the cancer is solid or hematopoietic-derived tumor type.

3. The method of claim 1, wherein the cancer is selected from the group consisting of neuroblastoma, melanoma, sarcoma, and renal cell cancers.

4. The method of claim 1, wherein the dead tumor cells are from a tumor in the subject.

5. The method of claim 1, wherein the dead tumor cells are from a cancer of the same type as the cancer in the subject.

6. The method of claim 5, wherein the dead tumor cells are from a cell line made from cells of a cancer of the same type as the cancer in the subject.

7. The method of claim 1, wherein the subject is a non-human animal or a human.

8. The method of claim 1, wherein the route of administration is selected from the group consisting of subcutaneous, intradermal, and subdermal.

9. The method of claim 1, further comprising administering one or more additional treatments to the subject.

10. The method of claim 9, further comprising administering one or more additional doses of the enhanced dendritic cells.

11. The method of claim 1, further comprising administering one or more additional doses of the enhanced dendritic cells.

12. The method of claim 1, further comprising identifying a subject having a cancer.

13. The method of claim 1, further comprising monitoring the subject for tumor growth, tumor regrowth, or survival.

* * * * *

UNITED STATES PATENT AND TRADEMARK OFFICE
CERTIFICATE OF CORRECTION

| | | |
|---|---|---|
| PATENT NO. | : 8,597,946 B2 | Page 1 of 1 |
| APPLICATION NO. | : 12/921708 | |
| DATED | : December 3, 2013 | |
| INVENTOR(S) | : Mule et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this
Fourteenth Day of April, 2015

Michelle K. Lee
*Director of the United States Patent and Trademark Office*